(12) United States Patent
Ma et al.

(10) Patent No.: US 7,998,936 B2
(45) Date of Patent: Aug. 16, 2011

(54) USE OF TIMOSAPONIN BLL IN THE PREPARATION OF A MEDICAMENT OR PRODUCT FOR THE PREVENTION AND TREATMENT OF STROKE

(75) Inventors: Baiping Ma, Beijing (CN); Quiping Xu, Beijing (CN); Yang Zhao, Beijing (CN); Chengqi Xiong, Beijing (CN); Dawei Tan, Beijing (CN)

(73) Assignee: Institute of Radiation Medicine, Academy of Military Medical Sciences, PLA, Beijing (CN)

( * ) Notice: Subject to any disclaimer, the term of this patent is extended or adjusted under 35 U.S.C. 154(b) by 328 days.

(21) Appl. No.: 11/587,880

(22) PCT Filed: Apr. 21, 2005

(86) PCT No.: PCT/CN2005/000553
§ 371 (c)(1),
(2), (4) Date: Sep. 29, 2008

(87) PCT Pub. No.: WO2005/105108
PCT Pub. Date: Nov. 10, 2005

(65) Prior Publication Data
US 2009/0075912 A1    Mar. 19, 2009

(30) Foreign Application Priority Data

Apr. 29, 2004  (CN) .......................... 2004 1 0037347
Mar. 25, 2005  (CN) .......................... 2005 1 0059466

(51) Int. Cl.
*A01N 45/00* (2006.01)
(52) U.S. Cl. ........................................ 514/26
(58) Field of Classification Search .................. None
See application file for complete search history.

(56) References Cited

FOREIGN PATENT DOCUMENTS

| CN | 1212966 | A | 4/1999 |
| CN | 1451384 | * | 11/2003 |
| CN | 1451384 | A | 11/2003 |

OTHER PUBLICATIONS

Yang, L.R., "Study on Chemical Component and Pharmacological Action of Anemarrhena Asphodeloides," (2002), pp. 207-210, vol. 24(4), *foreign medical science section of traditional Chinese medicine and Chinese material medicia*.
International Search Report for PCT/CN2005/000553 completed on Jun. 23, 2005.
Fu, Y., et al., "Pennogenin glycosides with a spirostanol structure are strong platelet agonists: structural requirement for activity and mode of platelet agonist synergism," *Journal of Thrombosis and Haemostasis*, 2007, vol. 6, pp. 524-533.
Guo, L., et al., "Active pharmaceutical ingredients and mechanisms underlying phasic myometrial contractions stimulated with the saponin extract from *Paris polyphylla* Sm. var. *yunnanensis* use for abnormal uterine bleeding," *Human Reproduction*, 2008, vol. 23(4), pp. 964-971.
Ma, B., et al., "New Spirostanol Glycosides from *Anemarrhena aspholdeloides*," *Planta Med.*, 1997, vol. 63, pp. 376-379.
Ma, et al., "Studies on the Furostanol Saponins From *Anemarrhena Asphodeloides* Bunge," *Acta Pharmaceutica Sinica*, 1996, vol. 31(4), pp. 271-277. Abstract Only.
Saito, S., et al., New Steroidal Saponins from the Rhizomes of *Anemarrhena asphodeloides* Bunge (Liliaceae), *Chem. Pharm. Bull.*, 1994, vol. 42(11), pp. 2342-2345.
Wang, et al., G., "Effect of timosaponin A-III from *Anemarrhenae asphodeloides* Bunge (Liliaceae), on calcium mobilization in vascular endothelial and smooth muscle cells on vascular tension," *Life Sciences*, 2002, vol. 71, pp. 1081-1090.
Zhang, J., et al., "Effect of Steroidal Saponins of *Anemarrhenae Rhizoma* on Superoxide Generation in Human Neutrophils," *Biochemical and Biophysical Research Communications*, 1999, vol. 259, pp. 636-639.
Zhang, J., et al., "Effect of six steroidal saponins isolated from anemarrhenae rhizome on platelet aggregation and hemolysis in human blood," *Clinica Chimica Acta*, 1999, vol. 289, pp. 79-88.
Zhiyun, M., et al., "Timosaponins E1 and E2," *Acta Pharmaceutica Sinica*, 1998, vol. 33(9), pp. 693-696. Abstract Only.
Zhiyun, M., et al., "A New Steroidal Saponin from Anemarrhena asphodeloides Bge," *Journal of Shenyang Pharmaceutical University*, 1998, vol. 15(4), pp. 254-255. Abstract Only.

* cited by examiner

*Primary Examiner* — Traviss C McIntosh, III
(74) *Attorney, Agent, or Firm* — Alston & Bird LLP

(57) ABSTRACT

The invention disclosed the use of timosaponin BII in the preparation of a medicament or product for the prevention and treatment of stroke. The experiments prove that timosaponin BII can improve the neurological symptoms of cerebral ischemic rat, reduce infarct size, relieve brain water edema, improve hemorheology, reduce inflammatory injury of cerebral ischemia.

2 Claims, No Drawings

USE OF TIMOSAPONIN BLL IN THE PREPARATION OF A MEDICAMENT OR PRODUCT FOR THE PREVENTION AND TREATMENT OF STROKE

TECHNICAL FIELD

The present invention relates to use of timosaponin BII, in particular the use of timosaponin BII in the preparation of a medicament or product for the prevention and treatment of stroke (apoplexy).

BACKGROUND ART

Stroke (apoplexy) involves sudden loss of neural function due to disturbance in cerebral perfusion owing to intracranial and extracranial angiemphraxis or angiorrhexis, which seriously harms the health of the aged and middle-aged as a main cause of disability and death. About one third of patients attacked by the disease will develop to death; even survivors will lose their work ability or self-care ability due to sequelae such as hemiplegia and aphasia. At present, there are two treatments available for stroke: One is to relieve deficiency of oxygen and glucose in arteries via increasing blood flow; the other is to protect neuron through blocking neuron death caused by cerebral ischemia and excitotoxicity. Clinically used neuron protective agents include calcium channel blockers, glutamate receptor antagonists and NMDA antagonists etc. However, in view of the high morbidity, mortality and disability rates, there are few drugs developed for prevention and treatment of stroke, which is far from enough to meet clinical need.

Rhizome Anemarrhenae as an herbal medicine, is rhizome of Anernarrhena asphodeloides Bge, anemarrhena of family Liliaceae, which is mainly produced in Hebei, Inner Mongolia, Shanxi and northeast China. In traditional Chinese medicine, it is used as a bitter cold heat-clearing drug with effects of relieving exogenous febricity, hyperpyrexia and polydipsia, lung-heat and dry cough, osteopyrexia and fevers calor intemus and diabetes and dryness of the intestine and constipation. Essential component of anemarrhenae is steroidal saponins. To date, 32 kinds of steroidal saponins and sapogenin isolated from anemarrhenae have been reported as well as other components such as chromocor, oligosaccharide, polysaccharides, fatty acid, etc. Kawasaki et al. first isolated the timosaponin BII in 1963, but did not elucidate its chemical structure. Seiji Nagumo et al. elucidated the chemical structure of timosaponin BII first in 1991 (Seiji NAGUMO et al, J. Pharm. (Japanese), 1991: 111(1); 306-310). From then on, extraction and activity determination of Timosaponin BII were reported by Noboru Nakashima (NOBORU NAKASHIMA et al, Journal of Natural Products, 1993; 56(3): 345-350), Ma Bai ping (Ma B P et al., Yao Xue Xue Bao, 1996: 31(4): 271-277), Masayasu Kimula (Masayasu KIMURA et al, Biol. Pharm. Bull, 1996; 19(7); 926-931), Jianying Zhang (Jianying ZHANG et al, Clinica Chimica Acta, 1999; 289: 79-88) successively.

Timosaponin BII, also called Prototimosaponin AIII, is the essential component of anemarrhenae. Its chemical name is (25S)-26-O-β-D-glucopyranosyl-22-hydroxy-5β-furostane-3β,26-diol-3-O-β-D-glucopyranosyl(1→2)-β-D-galactopyranoside, with structural formula shown as follow:

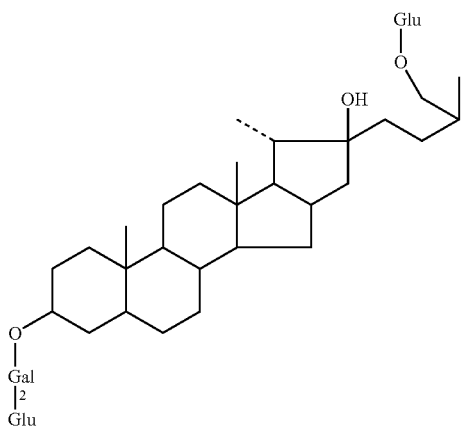

The pharmacological activities of Timosaponin BII that have been reported mainly include:
1. Hypoglycemic activity. Timosaponin BII can lower blood sugar level in streptozocin-induced diabetic mouse without promoting absorption of glucose and release of insulin. The mechanism of reducing blood glucose is supposed to be the inhibition of liver sugar decomposition (NOBORU NAKASHIMA et al, Journal of Natural Products, 1993; 56(3): 345-350)
2. Inhibition of platelet aggregation. Timosaponin BI possesses activity of obviously inhibiting platelet aggregation and prolonging clotting time (Jianying ZHANG et al, Clinica Chimica Acta, 1999; 289:79-88).
3. Clearance of free radicals. Observation via paramagnetic method shows that timosaponin BII can clear 57% free radicals generated from Fenton reaction system (Ma B P, et al. Yao Xue Xue Bao, 1996; 31(4): 271-277).
4. Anti-dementia activity. Ma Bai ping et al. reported that timosaponin BII have preventive and therapeutic effect against senile dementia (Chinese Patent Application Publication No. CN1212966, Application No. 97119680.X).

Chen Wan sheng et al. reported the use of total Timosaponins in preparation of medicaments for prevention and treatment of stroke (Chinese Patent Application Publication No. CN1451384A Application No. 03116824.8). The total timosaponins disclosed therein are characterized by a sum of contents of timosaponins BII, E, B, AIII of ≧50%.

CONTENTS OF THE INVENTION

After years of intensive research, the present inventors first found and confirmed the activity of timosaponin BII alone in the prevention and treatment of stoke. Said compound can significantly ameliorate neurological symptoms in ischemic rats, reduce size of cerebral infarction and relieve the extent of cerebral edema; and significant improve the hemorheology in the model animals and reduce inflammatory injury caused by cerebral ischemia.

Therefore, the present invention relates to the use of timosaponin BII in the preparation of a medicament or product for the prevention or treatment of stroke.

The present invention also relates to a pharmaceutical composition or product for the prevention or treatment of stroke, comprising timosaponin BII as the active ingredient and a pharmaceutically acceptable carrier or excipient.

According to the present invention, timosaponin BII is used in a substantially pure form, e.g. the purity of timosaponin BII being ≧90%.

According to the present invention, the pharmaceutical composition or product comprising timosaponin BII can be administered through various routes, and formulated into various dosage forms, e.g. oral dosage forms, such as a tablet, capsule, solution, suspension; parenteral dosage forms, such as an injection, ointment, patch, etc. According to the present invention, continuous administration of timosaponin BIT (20 mg/kg and 40 mg/kg) for 7 days could significantly lower the neurological symptom score in rats having middle cerebral artery (MCA) thrombosis, and significantly reduce the cerebral infarct size in the model rats; administration at 40 mg/kg could significantly reduce the water content of brain when compared with the model group ($p<0.05$, $p<0.01$).

According to the present invention, subcutaneous injection of adrenaline plus ice-water immersion method could lead to an acute blood stasis rat model, and administration of timosaponin BII (10 mg/kg, 20 mg/kg, 40 mg/kg) could significantly reduce the whole blood and plasma viscosities under high, middle and low shear rates, as compared with the model group ($p<0.05$, $p<0.01$). Timosaponin BII at 40 mg/kg could significantly improve the deformation ability of erythrocytes, and reduce the erythrocyte agglutination index, as compared with the model group ($p<0.05$, $p<0.01$).

The embolic thread method was employed in the preparation of cerebral-ischemia-reperfusion rat model, and ELISA was used to determine the levels of IL-1$\beta$, TNF-$\alpha$, IL-10 and TGF-$\beta$ in each group. The results showed that timosaponin BII had significant protective effect against the inflammatory responses in ischemia-reperfusion model rats.

To sum up, timosaponin BII has utility in the prevention and treatment of stroke.

MODES OF CARRYING OUT THE INVENTION

The following examples are intended to further illustrate the invention, but not meant to be limiting in any way.

EXAMPLE 1

Effect of Timosaponin BII on Ischemic Cerebral Injury in FeCl$_3$-Induced Middle Cerebral Artery Thrombosis (MCAT) Rats
I. Method
1. Effect of Timosaponin BII on Neurological Symptoms and Cerebral Infarct Size in Middle Cerebral Artery Thrombosis Rats 1.1. Grouping and Dosing The experimental animals were randomly divided into 6 groups, i.e. MCAT model group, sham-operation group, hydergine (0.6 mg/kg) group, timosaponin BII 10 mg/kg group, 20 mg/kg group and 40 mg/kg group. Continuous administration of the drugs by gavage was performed for 7 days with daily volume of 5 ml/kg. The operation was carried out one hour after drug administration on the seventh day. The MCAT model and sham-operation groups were given the same volume of a 0.5% CMC solution.

1.2. Preparation of MCA Thromboembolia-Induced Ischemic Cerebral Injury Model in Rats Tamura and Liu's methods were used with modifications to prepare the model. Rats were anesthetized by intraperitoneal injection of 10% chloral hydrate (0.35 g/kg); and fixed with right arm reclining. An arc incision of about 1.5 cm in length was made at the midpoint between the link of paropia and external auditory canal and temporalis was removed to expose the temporal bone. An opening in the bone of about 2.5 mm in diameter was made by a bur drill at the junction of malar bone and quama temporalis 1 mm cephalically under stereoscopic microscope, and residues were cleaned up to expose the middle cerebral artery (located between the olfactory tract and inferior cerebral vein). The surrounding-tissues were protected with a piece of plastic film. A small piece of quantitative filter paper, which had absorbed 10 µL of a 50% ferric chloride solution, was applied on this segment of middle cerebral artery. The filter paper was removed after 30 min, and local tissues were rinsed with normal saline solution, followed by suture layer by layer. Then the experimental rats were put back to rearing cage. The temperature was controlled at 24° C. For the sham-operation group, the operation procedures were the same as the model group except for the application of the ferric chloride solution.

1.3. Assessment of Neurological Symptom Score

The experimental animals were tested for behaviors 6 h and 24 h after operation according to the Sederson's method with modifications. Criteria: ① The tail of the rat was lifted to observe the flexibility of the forelimb, with both forelimbs symmetrically stretching forward scored as 0, and occurrence of any or all of shoulder inflexion, elbow inflexion, shoulder intorsion in the contralateral fore-limb opposite to the operation side scored as 1. ② The animal was placed on a plane, and its shoulders were pushed to the opposite direction to check resistance, Equivalency and strong resistance in both sides was scored as 0, and reduction in resistance in the contralateral side was scored as 1. ③ Both forelimbs of the rat were placed on wire gauze to observe the muscular tension. Equivalency and strong tension in both sides was scored as 0, and reduction in muscular tension in the contralateral forelimb was scored as 1. ④ The tail of the rat was pulled up, and the animal exhibiting incessant rotations in the direction opposite to the operation side was scored as 1. According to the criteria above, the full score is 4, and the higher the score is, the more serious the behavior disorder of the animal is.

1.4. Determination of Cerebral Infarct Size

After behavior assessment, the animals were decapitated to remove the brains. The olfactory bulb, cerebellum and lower brain stem were removed, and the remaining part was cut into 5 coronal sections below 4° C. The sections were immediately placed into a TTC staining solution (containing 1.5 m 4% TTC, 0.1 ml 1M K$_2$HPO$_4$ and water (balance) per 5 ml staining solution), followed by incubation in dark at 37° C. for 30 min. Then, the sections were transferred into a solution of 10% formaldehyde and incubated in dark for 24 h. After staining, the non-ischemic areas were rose red, and the infracted areas were white. The white tissues were carefully collected and weighed. The extent of cerebral infarction was expressed as a percentage (%) of infracted tissue to the weight of total brain and also to the affected side of brain.

2. Effect of Timosaponin BII on Water Content in Brain Tissues in Middle Cerebral Artery Thrombosis (MCAT) Rats 2.1. Grouping, Dosing and Modelling Methods (See 1 Above.)

2.2. Determination of Water Content in Brain Tissues

The rats were decapitated 24 h after operation, and the brain were removed and separated into left and right hemispheres. Filter paper was used to blot surface and the wet weight of each hemisphere was weighed, respectively. Then, drying of the brain tissues at 105° C. was performed for 48 h followed by accurate weighing of the dry weight. The water content of the brain was calculated according to the following formula:

Water content of brain=(wet weight−dry weight)/wet weight×100%

3. Statistical Analysis

The experimental data were expressed as $\bar{x}\pm s$. The results were analysed using SPSS software and t-test was used to perform comparison among groups.

II. Results

1. Effect of Timosaponin BII on Neurological Symptoms and Cerebral Infarct Size of Middle Cerebral Artery Thrombosis Rats The results are shown in Table 4-1 below.

TABLE 4-1

Effect of timosaponin BII on neurological symptoms and cerebral infarct size of middle cerebral artery thrombosis rats ($\bar{x} \pm s$)

| Group | Dosage mg/kg | n | cerebral infarct size percentage to total brain (%) | percentage to affected side (%) | neurological symptomatic score 6 h | 24 h |
|---|---|---|---|---|---|---|
| Sham-operation | — | 12 | 0 ± 0 | 0 ± 0 | 0.08 ± 0.29 | 0.17 ± 0.39 |
| MCAT model | — | 12 | 4.58 ± 1.59$^{\triangle\triangle}$ | 8.76 ± 2.98$^{\triangle\triangle}$ | 2.73 ± 1.01$^{\triangle\triangle}$ | 2.55 ± 0.52$^{\triangle\triangle}$ |
| Hydergine | 0.6 | 11 | 1.98 ± 0.72** | 3.75 ± 1.38** | 1.91 ± 0.83* | 1.55 ± 0.69** |
| Timosaponin BII | 10 | 12 | 3.27 ± 1.74 | 6.35 ± 3.39 | 2.08 ± 0.67 | 2.08 ± 0.79 |
| Timosaponin BII | 20 | 11 | 2.92 ± 1.20* | 5.37 ± 2.20* | 1.82 ± 0.75* | 2.00 ± 0.45* |
| Timosaponin BII | 40 | 10 | 1.99 ± 1.20** | 3.88 ± 2.38** | 1.50 ± 0.71** | 1.90 ± 0.74* |

Notes:
$^{\triangle\triangle}P < 0.01$ vs. sham-operation group;
*P < 0.05,
**P < 0.01 vs. the model group.

The results indicate that as compared with the sham-operation group, animals of MCAT model group and each administration groups exhibited infarction focus and hemiplegia like symptoms to various extents. Timosaponin BII at 20 mg/kg and 40 mg/kg significantly reduced the cerebral infarct size and ameliorate neurological symptoms in model animals (P<0.05, P<0.01).

2. Effect of Timosaponin BII on Water Content in Brain Tissues in Middle Cerebral Artery Thrombosis (MCAT) Rats The results were shown in Table 4-2 below.

TABLE 4-2

Effect of timosaponin BII on water content in brain tissues in middle cerebral artery thrombosis (MCAT) rats ($\bar{x} \pm s$)

| Group | Dosage (mg/kg) | n | Water content of unaffected hemisphere (%) | Water content of affected hemisphere (%) |
|---|---|---|---|---|
| Sham-operation | — | 12 | 79.60 ± 0.49 | 79.59 ± 0.48 |
| MCAT model | — | 12 | 79.54 ± 0.80 | 81.12 ± 0.90$^{\triangle\triangle}$ |
| Nimodipine | 12 | 12 | 79.44 ± 0.41 | 80.37 ± 0.73* |
| Timosaponin BII | 10 | 12 | 79.51 ± 0.57 | 80.52 ± 0.69 |
| Timosaponin BII | 20 | 12 | 79.41 ± 0.38 | 80.46 ± 0.79 |
| Timosaponin BII | 40 | 12 | 79.47 ± 0.44 | 80.15 ± 0.99* |

Notes:
$^{\triangle\triangle}P < 0.01$ vs. the sham-operation group;
*P < 0.05 vs. the model group.

As indicated in the table above, timosaponin BII at 40 mg/kd significantly lowered the water content in the affected hemisphere and ameliorated cerebral edema in model rats (P<0.05).

Discussion and Summary

Middle cerebral artery thrombosis model is a common animal model of focal cerebral ischemia, which objectively simulates clinical circumstance of cerebral infarction in Middle cerebral artery, with advantages of easy control for local conditions and replication, similarity to the course of clinical cerebral apoplexy and fixed location of thrombus. As the results show, 6 h or 24 h after operation, hemiplegia like symptoms, increase of water content in cerebral thrombosis side and marked cerebral infarction (by TTC staining) were observed. As compared with the sham-operation group timosaponin BII at 20 mg/kg and 40 mg/kg group significantly reduced cerebral infarct size and ameliorate neurological symptoms (P<0.05, P<0.01). Additionally, as compared with the model group, extent of cerebral edema in timosaponin BII 40 mg/kg group was significantly reduced (P<0.05). The results suggest that the drug has protective effect against ischemic cerebral injury.

EXAMPLE 2

Effect of timosaponin BII on Hemorheology in Acute Blood Stagnation Model Rats

I. Method

1. Grouping and Dosing

The experimental animals were randomly divided into 6 groups based on weight, i.e. model group, normal control group, nimodipine (12 mg/kg) group, timosaponin BII 10 mg/kg group, 20 mg/kg group and 40 mg/kg group. Continuous administration of the drugs by gavage was performed for 5 days with daily volume of 5 ml/kg. The normal control group and the model group were given the same volume of a 0.5% CMC solution.

2. Modelling Method

MAO Teng-min's methods were modified to prepare the model. Rats were subcutaneously injected with 0.8 mg/kg adrenaline twice at 1 h and 5 h after administration on the fifth day, and were placed into ice-water at 4° C. for 5 min at 2 h after the first injection of adrenaline.

3. Assessment of Whole Blood and Plasma Viscosities

Rats were anaesthetized by intraperitoneal injection of 10% chloral hydrate (0.35 g/kg) 1 h after the last administration. Blood was drawn from carotid artery and treated with 1% heparin. 0.8 ml of anticoagulated blood was tested in a blood viscometer and whole blood viscosity was represented by blood viscosity tested at high ($200\ S^{-1}$), middle ($30\ S^{-1}$), low ($5\ S^{-1}$) and low ($1\ S^{-1}$) shear rates. In addition, anticoagulated blood was centrifuged at 3000 rpm for 8 min to yield plasma as the supernatant, and 0.8 ml of plasma was test for plasma viscosity at $100\ S^{-1}$ in a blood viscometer.

4. Determination of Erythrocyte Aggregation and Deformability

To 40 μl of heparinized blood, 1 ml of deforming solution was added and mixed thoroughly. A sample of 0.8 ml was tested in an erythrocyte aggregation/deformability tester, and erythrocyte deformability was expressed as maximal erythrocyte deformation index and area under curve (SSS). Another 0.8 ml of anticoagulated blood was tested in an erythrocyte aggregation/deformability tester, and erythrocyte aggregation was expressed as maximal erythrocyte aggregation index (MAXD) and area under curve (SSS).

5. Statistical Analysis

The experimental data were expressed as $\bar{x} \pm s$. The results were analysed using SPSS software and t-test was used to perform comparison among groups.

II. Results

1. Effect of Timosaponin BII on Whole Blood and Plasma Viscosities in Acute Blood Stagnation Model Rats The results are shown in Table 10-1 below.

The results indicate that as compared with the blank control group, blood stagnation model rats showed significant increased erythrocyte aggregation index and decreased erythrocyte deformability index ($P<0.05$, $P<0.01$.) at 24 h after modelling. As compared with the model rats, rats in timosaponin BII 40 mg/kg group showed significant increase in erythrocyte deformability index and decrease in erythrocyte aggregation index ($P<0.05$, $P<0.01$), III. Discussion and Summary Hemorheology is a science concerning blood fluidity, aggregation, coagulability and blood cell deformability. Hemorheological parameters such as whole blood specific viscosity, plasma specific viscosity, erythrocyte aggregation index and fibrinogen may change in patients suffering from ischemic cerebrovascular disease. Therefore, improvements in hemorheology, including decrease of blood viscosity and erythrocyte aggregation, and increase of erythrocyte deform-

TABLE 10-1

Effect of timosaponin BII on whole blood and plasma viscosities in acute blood stagnation model rats ($\bar{x} \pm s$)

| Group | Dosage mg/kg | n | Whole blood viscosity 200 $S^{-1}$ | 30 $S^{-1}$ | 5 $S^{-1}$ | 1 $S^{-1}$ | Plasma viscosity (100 $S^{-1}$) |
|---|---|---|---|---|---|---|---|
| Blank control | — | 13 | 3.81 ± 0.42 | 5.42 ± 0.60 | 10.34 ± 1.41 | 25.74 ± 4.64 | 1.33 ± 0.11 |
| Model | — | 14 | 5.05 ± 0.74$^{\Delta\Delta}$ | 7.56 ± 1.18$^{\Delta\Delta}$ | 15.52 ± 3.28$^{\Delta\Delta}$ | 41.48 ± 11.64$^{\Delta\Delta}$ | 1.53 ± 0.11$^{\Delta\Delta}$ |
| Nimodipine | 12 | 12 | 4.51 ± 0.55* | 6.47 ± 0.92* | 12.34 ± 2.58** | 30.45 ± 8.74* | 1.41 ± 0.14* |
| Timosaponin BII | 10 | 10 | 4.45 ± 0.71 | 6.10 ± 0.85** | 11.02 ± 1.38** | 27.03 ± 4.64** | 1.40 ± 0.10** |
| Timosaponin BII | 20 | 13 | 4.49 ± 0.70 | 6.55 ± 0.93* | 12.91 ± 1.82* | 33.13 ± 5.70* | 1.36 ± 0.10** |
| Timosaponin BII | 40 | 12 | 4.42 ± 0.38* | 6.45 ± 0.60** | 12.46 ± 1.33** | 31.21 ± 4.29** | 1.38 ± 0.12** |

Notes:
$^{\Delta\Delta}P < 0.01$ vs. the blank control group;
*$P < 0.05$,
**$P < 0.01$ vs. the model group.

The results indicate that as compared with the normal control group, whole blood and plasma viscosities significantly increased in blood stagnation model rats at 24 h after modelling ($P<0.01$). Timosaponin BII at 10 mg/kg, 20 mg/kg and 40 mg/kg significantly lowered whole blood and plasma viscosities at high, middle and low shear rates in model rats ($P<0.05$, $P<0.01$).

2. Effect of Timosaponin BII on Erythrocyte Aggregation and Deformability in Acute Blood Stagnation Model Rats The results are shown in Table 10-2 below.

ability, are crucial in prevention and treatment of ischemic cerebrovascular disease. In our study, rats were subcutaneously injected with a large dose of adrenaline to simulate anger and anxious status and were placed in ice water to simulate chill status. In this way, an acute blood stagnation model with features of viscous, thick, coagulated and aggregated blood was replicated. From the results it is shown that timosaponin BII could significantly inhibit erythrocyte aggregation, increase erythrocyte deformability and reduce whole blood and plasma viscosities at high, middle and low

TABLE 10-2

Effect of timosaponin BII on erythrocyte aggregation and deformability in acute blood stagnation model rats ($\bar{x} \pm s$)

| Group | Dosage (mg/kg) | n | Erythrocyte aggregation MAXD | SS | Erythrocyte deformability MAXDI | SSS |
|---|---|---|---|---|---|---|
| Blank Control | — | 13 | 0.52 ± 0.13 | 94.97 ± 25.97 | 0.71 ± 0.03 | 365.02 ± 20.48 |
| Model | — | 14 | 0.89 ± 0.11$^{\Delta\Delta}$ | 176.52 ± 19.74$^{\Delta\Delta}$ | 0.69 ± 0.02$^{\Delta}$ | 349.22 ± 10.59$^{\Delta}$ |
| Nimodipine | 12 | 12 | 0.80 ± 0.09* | 160.38 ± 16.50* | 0.70 ± 0.03 | 353.92 ± 15.83 |
| Timosaponin BII | 10 | 10 | 0.94 ± 0.14 | 186.67 ± 28.85 | 0.72 ± 0.05 | 363.88 ± 19.58 |
| Timosaponin BII | 20 | 13 | 0.81 ± 0.26 | 163.04 ± 50.23 | 0.71 ± 0.05 | 363.97 ± 27.87 |
| Timosaponin BII | 40 | 12 | 0.76 ± 0.14* | 152.78 ± 28.11* | 0.73 ± 0.03** | 374.26 ± 15.82** |

Notes:
$^{\Delta}P < 0.05$,
$^{\Delta\Delta}P < 0.01$ vs. the blank control group;
*$P < 0.05$,
**$P < 0.01$ vs. the model group.

EXAMPLE 3

Effect of Timosaponin BII on Inflammatory Factors in Brain Tissues in Cerebral Ischemia-Reperfusion Rats The embolic thread method was employed in the preparation of cerebral ischemia-reperfusion rat model, and ELISA was used to determine the levels of IL-1β, TNF-α, IL-10 and TGF-β in each group so as to investigate the protective effect of timosaponin BII on inflammatory factors in cerebral ischemia-reperfusion model rats.

I. Method

1. Grouping and Dosing

The rats were randomly divided into 6 groups based on body weight, i.e. the sham-operation group, model group, nimodipine (12 mg/kg) group, timosaponin BIat 10 mg/kg group and 40 mg/kg group. All drugs were formulated with 0.5% CMC. Rats of each group were used for experiments after 2 days' observation and raising. Continuous administration of the drugs by gavage was performed for 5 days with a daily volume of 10 ml/kg. The sham-operation group and model group were given the same volume of a 0.5% CMC solution once a day. The operation was carried out one hour after drug administration in the morning of the fifth day.

2. Modelling Method

Middle cerebral artery obstruction (MCAO) model was prepared as described by Koizumi and Nagasawa. Rats were anesthetised by intraperitoneal (ip) injection with 10% chloral hydrate at 0.35 g/kg and were fixed in supine position. After local sterilization, the operation began. The right common carotid artery (CCA), right internal carotid artery (ICA) and external carotid artery (ECA) were separated and threads were embedded for future use. The ECA and CCA were ligated. Soon after the distal end of the ICA was closed by an artery clamp, a incision was made at the bifurcation of the ECA and ICA, and one nylon thread with one end heated to become bulb-shaped (0.25 mm in diameter, marked at 2 cm from the bulb end, and the anterior end of the embolic thread was treated with paraffin for future use) was inserted. After the thread was inserted into the ICA, the thread and the ICA inlet were slightly ligated, and then the artery clamp was released. The nylon thread was inserted further into the ICA and was slightly withdrawn when there was a little resistance, until it reached the depth of about 18.5±0.5 mm, causing MCA obstruction and hence cerebral-ischemia. The inlet was ligated again, leaving 1 cm long nylon thread outside. The muscles and skin were sutured, and the rats were injected intraperitoneally with gentamicin sulfate at 0.4 ml/per rat. After 3 h, the thread end was gently pulled outwards until there was resistance, leading to MCA reperfusion. Thus, the modelling was completed. In the sham-operation group, only right CCA was ligated, with no incision and thread insertion.

The inclusion criteria: 3 h after the ischemia, animals that showed signs of contralateral forelimb twisting, walking around in a circular path or falling down in a contralateral direction while walking were included. Animals that did not show these signs or were still unconscious after 3 h were excluded.

3. Preparation of Tissue Homogenates

The animals were decapitated 3 h after ischemia and 21 h after reperfusion. The olfactory bulb, cerebellum and low brain stem were removed and the rest of the right hemisphere was homogenized in normal saline at 4° C. to a concentration of 10%.

4. ELISA Assays for IL-1β, TNF-α IL-10 and TGF-β

(1) Establishment of Standard Curve

Eight standard wells were established, and each was added 100 ul of sample dilution solution. To the first well was added 100 ul of standard, mixed well, and then 100 ul was pipetted to the second well. This double diluting process was repeated until the seventh well. Finally, 100 ul was pipetted from the seventh well and discarded so that the volume in each well was 100 ul. The eighth well served as the blank control.

(2) Loading 150 ul of sample was added to each sample well.

(3) The reaction plate was mixed well and placed at 370 for 120 min.

(4) Plate Washing

The reaction plate was thoroughly washed with washing solution 4-6 times, and blotted with filter paper.

(5) To each well was added 50 ul of a first antibody working solution, and the plate was placed at 37° for 60 min.

(6) Plate washing: see above.

(7) To each well was added 100 ul of an enzyme-conjugated antibody working solution and the plate was placed at 37° C. for 60 min.

(8) Plate washing: see above.

(9) To each well was added 100 ul of a substrate working solution, and the plate was placed in dark at 37° for 5-10 min.

(10) To each well was added 1 drop of a stop solution and was mixed well.

(11) The absorbance at 492 nm was read.

5. Result Calculation

Calculation was done after subtracting the blank value from all OD values. The OD values for the standard at 1000, 500, 250, 125, 62, 31, 16, and 0 PG/ml were plotted on a semi-log paper, to obtain a standard curve. The level of the corresponding inflammatory factor could be determined from the standard curve based on the OD value of the sample, 6. Statistical Analysis The experimental data were expressed as $\bar{x}\pm s$. The results were analyzed using SPSS software and t-test was used to perform comparison among groups.

II. Results

Effect of Timosaponin BII on Inflammatory Factors in Cerebral Ischemia-Reperfusion Rats

TABLE

Effect of Timosaponin BII on levels of IL-1β, TNF-α, IL-10 and TGF-β in ischemia-reperfusion rats ($\bar{x} \pm s$)

| Group | Dosage mg/kg | n | IL-1β (Pg/ml) | TNFα (Pg/ml) | IL-10 (Pg/ml) | TGF-β (Pg/ml) |
|---|---|---|---|---|---|---|
| Sham-operation | — | 8 | 9.42 ± 0.94 | 7.91 ± 0.36 | 3.55 ± 3.03 | 12.89 ± 4.51 |
| Model | — | 8 | 10.95 ± 0.74$^{\Delta\Delta}$ | 8.74 ± 0.70$^{\Delta\Delta}$ | 16.75 ± 3.45$^{\Delta\Delta}$ | 17.69 ± 2.84$^{\Delta}$ |

TABLE-continued

Effect of Timosaponin BII on levels of IL-1β, TNF-α, IL-10 and TGF-β in ischemia-reperfusion rats ($\bar{x} \pm s$)

| Group | Dosage mg/kg | n | IL-1β (Pg/ml) | TNFα (Pg/ml) | IL-10 (Pg/ml) | TGF-β (Pg/ml) |
|---|---|---|---|---|---|---|
| Nimodipine | 12 | 8 | 9.01 ± 0.81** | 7.92 ± 0.56* | 4.98 ± 3.54** | 12.01 ± 2.54** |
| Timosaponin BII | 10 | 8 | 9.70 ± 0.30** | 8.44 ± 0.62 | 14.49 ± 11.78 | 12.70 ± 3.57* |
| Timosaponin BII | 40 | 8 | 7.98 ± 0.80** | 7.65 ± 0.61** | 11.19 ± 5.16* | 10.30 ± 3.79** |

Notes:
ΔP < 0.05,
ΔΔP < 0.01 vs. the sham-operation group;
*P < 0.05,
**P < 0.01 vs. the model group The experimental results indicated that as compared with the sham-operation group, the levels of pro-inflammatory factors IL-1β and TNF-α in brain tissue of cerebral ischemia-reperfusion model rats significantly increased, and the levels of protective inflammatory factors IL-10 and TGF-β also increased significantly, and the differences were statistically significant. Positive control of Nimodipine and timosaponin BII at 40 mg/kg significantly reduced the levels of these inflammatory factors and thus had obvious protective effects in the inflammation responses in ischemia-reperfusion model rats.

The invention claimed is:

1. A method for treating apoplexy (stoke) or ameliorating symptoms of apoplexy, the method consisting of the step of administering a therapeutically effective amount of timosaponin BII to a subject having apoplexy.

2. The method of claim 1, wherein the purity of timosaponin BII is at least 90%.

* * * * *

UNITED STATES PATENT AND TRADEMARK OFFICE
CERTIFICATE OF CORRECTION

PATENT NO. : 7,998,936 B2  
APPLICATION NO. : 11/587880  
DATED : August 16, 2011  
INVENTOR(S) : Ma et al.

Page 1 of 1

It is certified that error appears in the above-identified patent and that said Letters Patent is hereby corrected as shown below:

On Title of the patent, in the Title Item (54), "BLL" should be --BII--;

Col. 1, line 37, "Anernarrhena" should be --Anemarrhena--;

Col. 1, line 43, "fevers calor" should be --fever, calor--;

Col. 1, line 44, "intemus" should be --internus--;

Col. 2, lines 1-17, replace the current formula with the below formula:

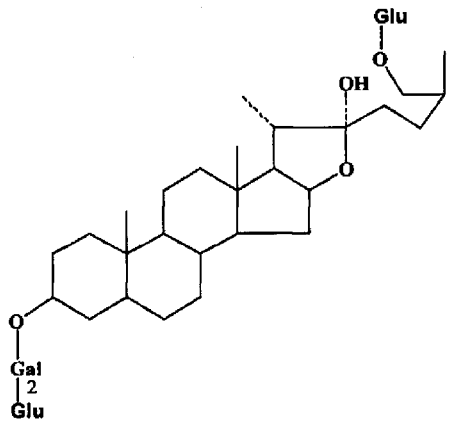

Col. 2, line 29, "BI" should be --BII--;

Col. 4, line 17, "Sederson's" should be --Bederson's--; and

Col. 12, Claim 1, line 18, "(stoke)" should be --(stroke)--.

Signed and Sealed this  
Twenty-second Day of November, 2011

David J. Kappos  
*Director of the United States Patent and Trademark Office*